(12) United States Patent
Berthelot et al.

(10) Patent No.: US 12,383,918 B2
(45) Date of Patent: Aug. 12, 2025

(54) FLUID DISPENSER DEVICE

(71) Applicant: APTAR FRANCE SAS, Le Neubourg (FR)

(72) Inventors: Jonathan Berthelot, Le Vaudreuil (FR); Olivier Deschamps, Romilly sur Andelle (FR)

(73) Assignee: APTAR FRANCE SAS, Le Neubourg (FR)

( * ) Notice: Subject to any disclaimer, the term of this patent is extended or adjusted under 35 U.S.C. 154(b) by 929 days.

(21) Appl. No.: 17/205,112

(22) Filed: Mar. 18, 2021

(65) Prior Publication Data

US 2021/0299690 A1  Sep. 30, 2021

(30) Foreign Application Priority Data

Mar. 30, 2020 (FR) ...................................... 2003151

(51) Int. Cl.
*B05B 11/10* (2023.01)
*A61M 15/00* (2006.01)
(Continued)

(52) U.S. Cl.
CPC ..... *B05B 11/1091* (2023.01); *A61M 15/0045* (2013.01); *A61M 15/0065* (2013.01); *A61M 15/08* (2013.01); *B05B 11/0078* (2013.01)

(58) Field of Classification Search
CPC ............ B05B 11/0078; B05B 11/1091; A61M 15/0045; A61M 15/0065; A61M 15/18
(Continued)

(56) References Cited

U.S. PATENT DOCUMENTS

| 4,475,905 A | 10/1984 | Himmelstrup |
| 5,404,871 A * | 4/1995 | Goodman ............. A61M 15/00 128/200.14 |

(Continued)

FOREIGN PATENT DOCUMENTS

| DE | 195 45 226 C1 | 6/1997 | |
| DE | 19545226 | * 6/1997 | ............ A61M 11/00 |

(Continued)

OTHER PUBLICATIONS

French Preliminary Search Report and Written Opinion for FR 2003151 dated Dec. 10, 2020.

*Primary Examiner* — Chee-Chong Lee
(74) *Attorney, Agent, or Firm* — Sughrue Mion, PLLC

(57) ABSTRACT

A fluid dispenser device comprising: a reservoir (10) containing one or more doses of fluid; a resilient element (20), such as a spring, for urging said reservoir (10) to move axially between a rest position and at least one actuated position; and blocking means (30; 51, 53, 55) for preventing said reservoir (10) from moving axially; said blocking means being movable manually in a direction that is different from the direction of said axial movement of the reservoir (10) so as to allow said reservoir (10) to move axially; said blocking means comprising a plate (30) provided with an opening (31) comprising a first opening portion (31*a*) of smaller size, and a second opening portion (31*b*) of larger size, said first and second opening portions (31*a*, 31*b*) being interconnected, said plate (30) being movable radially between a blocking position in which said first opening portion (31*a*) co-operates with said reservoir (10) so as to block it axially, and a non-blocking position in which said second opening portion (31*b*) co-operates with said reservoir (10) so as to allow said reservoir (10) to move axially under the effect of said resilient element (20).

8 Claims, 3 Drawing Sheets

(51) Int. Cl.
    *A61M 15/08*     (2006.01)
    *B05B 11/00*     (2023.01)

(58) Field of Classification Search
    USPC .......................................................... 239/321
    See application file for complete search history.

(56) References Cited

U.S. PATENT DOCUMENTS

| | | | | |
|---|---|---|---|---|
| 5,447,150 | A * | 9/1995 | Bacon | A61M 15/0096 |
| | | | | 128/200.14 |
| 5,544,647 | A * | 8/1996 | Jewett | A61M 15/0093 |
| | | | | 128/200.23 |
| 6,138,669 | A * | 10/2000 | Rocci, Jr. | A61M 15/0081 |
| | | | | 128/200.14 |
| 6,431,168 | B1 * | 8/2002 | Rand | A61M 15/0076 |
| | | | | 128/200.14 |
| 6,446,627 | B1 * | 9/2002 | Bowman | G06M 1/083 |
| | | | | 128/200.23 |
| 7,331,340 | B2 * | 2/2008 | Barney | G08B 5/36 |
| | | | | 128/200.23 |
| 2011/0033224 | A1 | 2/2011 | Schultz | |

FOREIGN PATENT DOCUMENTS

| | | | | |
|---|---|---|---|---|
| FR | 2 793 707 A1 | 11/2000 | | |
| WO | 03/020436 A1 | 3/2003 | | |
| WO | WO2003020436 | * | 3/2003 | ............. B05B 11/00 |

* cited by examiner

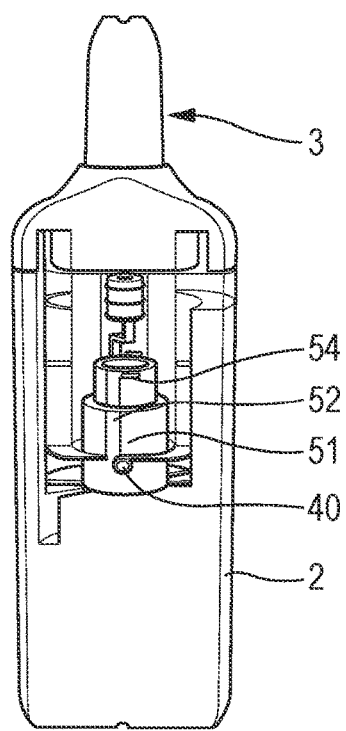
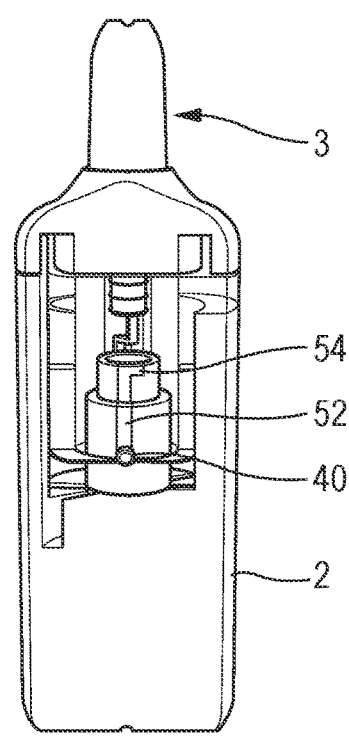
Fig. 9    Fig. 10
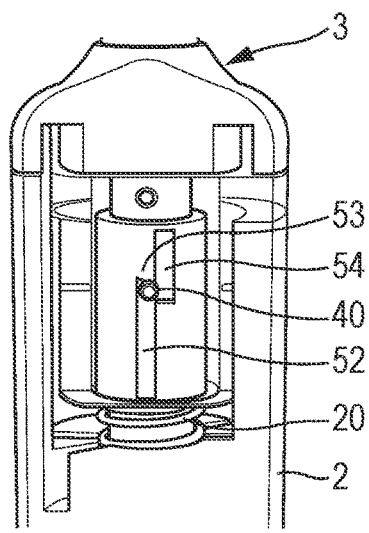
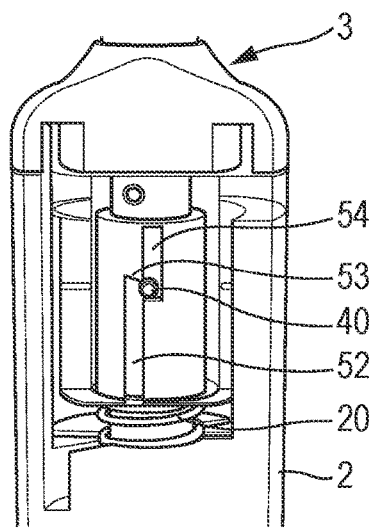
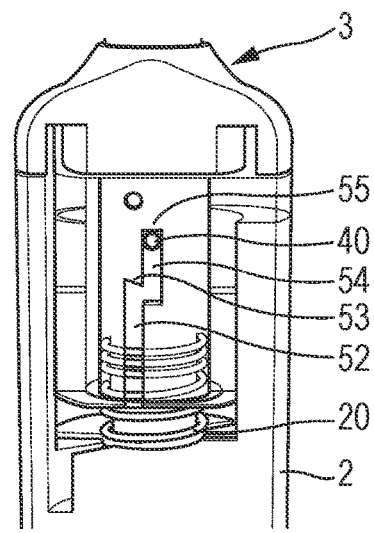
Fig. 11    Fig. 12    Fig. 13

FLUID DISPENSER DEVICE

The present invention relates to a fluid dispenser device, and more particularly to a fluid dispenser device for dispensing a limited number of doses, such as a single-dose device or a two-dose device.

Devices of the single-dose type or of the two-dose type are well known in the prior art and find some of their applications in the field of nasal pharmaceutical dispensers in which a single dose of fluid is to be dispensed into one nostril, or a respective dose is to be dispensed into each of the two nostrils for a two-dose device.

Document FR 2 761 281 discloses such a two-dose device. In order to use that device, the user places the dispenser orifice into a nostril and exerts axial pressure on the actuator element of the device. The axial pressure needs to be sufficiently high to overcome energy accumulation means in order to guarantee that each of the two doses is dispensed in full. While applying that relatively large axial force, it is difficult to control the positioning of the end of the device including the dispensing opening accurately in the nostril, and it can happen that the end of the head of the device comes into abutment with the end wall of the nostril, which can be troublesome and/or painful for the user. In addition, as a result of the device needing a predetermined minimum force in order to be actuated, it may be difficult to use for elderly people or for people with limited mobility who may have difficulty in exerting such force with the device placed in a nostril.

An object of the present invention is to provide a fluid dispenser device that does not present the above-mentioned drawbacks.

In particular, an object of the present invention is to provide a fluid dispenser device, such as a single-dose device or a two-dose device, that is simple and easy to use, and in which the dispensing of fluid is independent of the user's actuation force.

Another object of the present invention is to provide such a dispenser device that guarantees that a dose is dispensed in full on each actuation.

Another object of the present invention is to provide such a dispenser device that avoids any risk of injury during actuation.

Another object of the present invention is to provide such a device that is easier to assemble and fill, and in particular that enables a prefilled reservoir to be used, so that final assembly of the device does not need to take place in a sterile environment.

Another object of the present invention is to provide such a dispenser device that is simple and inexpensive to manufacture and to assemble.

The present invention thus provides a fluid dispenser device as described in claim 1. Advantageous embodiments are described in the dependent claims.

These advantages and characteristics and others of the present invention appear from the following detailed description of a plurality of variant embodiments, given by way of non-limiting examples, with reference to the accompanying drawings, and in which.

Figure 5:
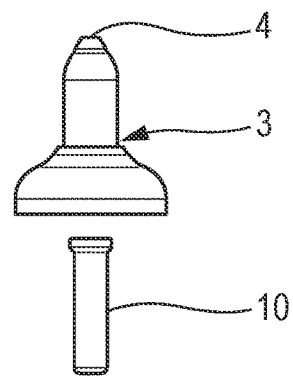
FIG. 5 is an exploded diagrammatic section view of a fluid dispenser device of the two-dose type in another embodiment, shown before assembly.
Figures 6, 7, 8:
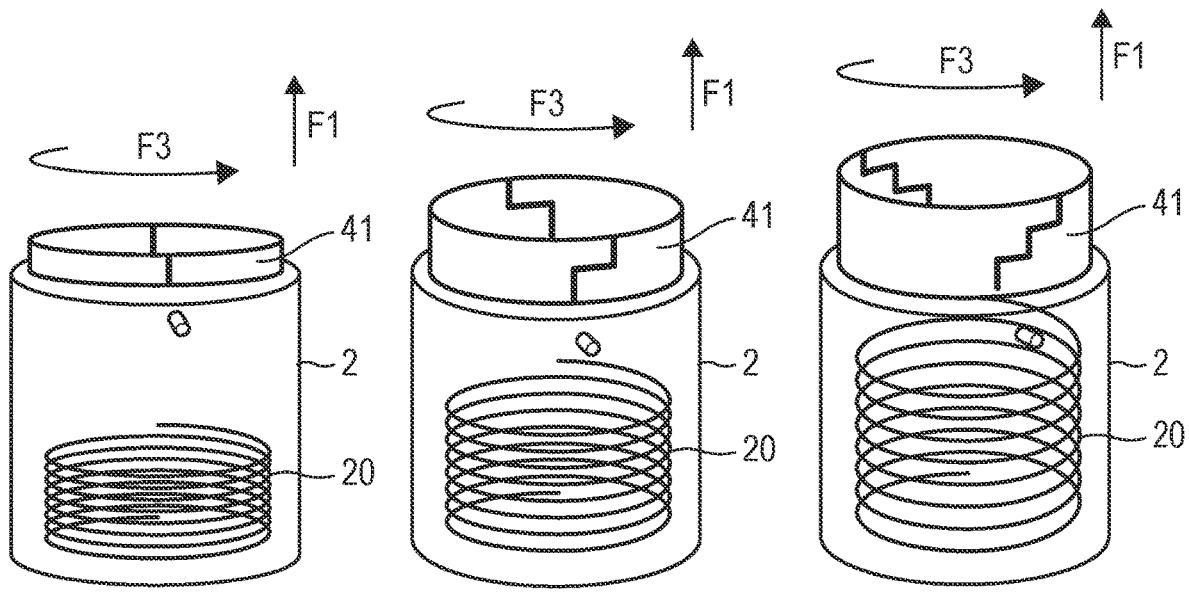

FIGS. 6 to 8 are diagrammatic and fragmentary representations of the FIG. 5 device, shown respectively before actuation, after the first dose has been dispensed, and after the second dose has been dispensed; and FIGS. 9 to 13 are diagrammatic and fragmentary views of the FIG. 5 device, shown respectively before actuation, before and after the first dose has been dispensed, and before and after the second dose has been dispensed.

In the description below, the terms "axial" and "radial" are relative to the longitudinal central axis of the device.

The present invention is described with reference to two variants embodiments that are shown in the drawings and that relate to fluid dispenser devices of the single-dose type and of the two-dose type, i.e. devices containing one or two doses of fluid to be dispensed, the fluid being for dispensing into the user's nose. Naturally, the present invention also applies to devices of the multi-dose type containing more than two doses, e.g. three or four doses. Furthermore, the present invention is not limited to dispensers of the nasal type.

FIGS. 1 to 4 show, in very diagrammatic manner, an embodiment of the present invention. In this embodiment, the device comprises a body 1 receiving a reservoir 10, preferably in the form of a tube. The reservoir 10 may be filled with the fluid to be dispensed, then closed in leaktight manner by an appropriate stopper (not shown), said prefilled reservoir 10 then being fitted in the body 1.

Figure 1:
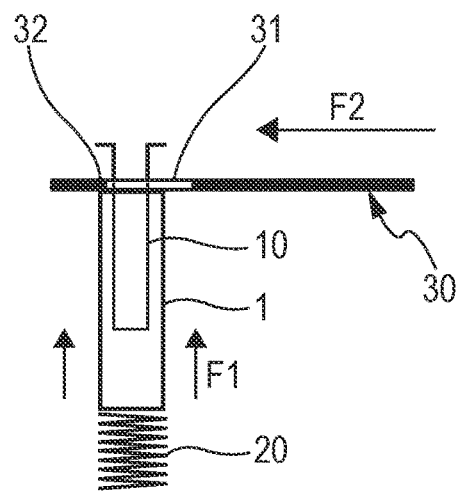
FIG. 1 is a diagrammatic and fragmentary section view of a fluid dispenser device of the single-dose type in an embodiment of the present invention, shown before the dose has been dispensed.
Figure 2:
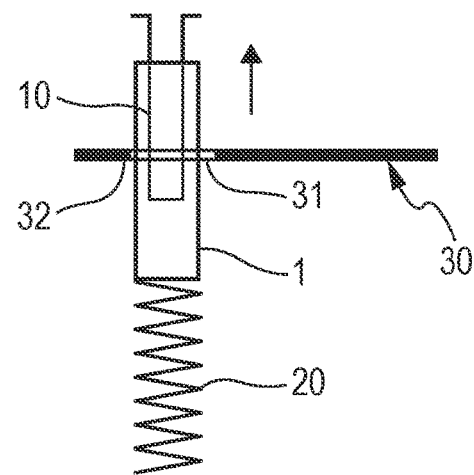
FIG. 2 is a view similar to the view in FIG. 1, shown after the dose has been dispensed.

The body 1 is axially movable, in the direction of arrow F1 in FIG. 1, between a rest position and an actuated position, and it co-operates with a resilient element 20, such as a spring, that urges said body 1 towards its actuated position.

Blocking means 30 that are movable between a blocking position and a non-blocking position hold the body 1 in its rest position. The blocking means 30 are movable manually by the user between the blocking position and the non-blocking position, said movement being performed in a direction that is different from the direction of axial movement of said body 1 between its rest and actuated positions.

In the example in FIGS. 1 to 4, the blocking means comprise a plate 30 that is movable radially in translation relative to said body 1, in the direction of arrow F2 in FIG. 1.

The plate 30 includes an opening 31 that receives the body 1. In the absence of a body, the opening 31 could receive the reservoir directly.

Figure 3:
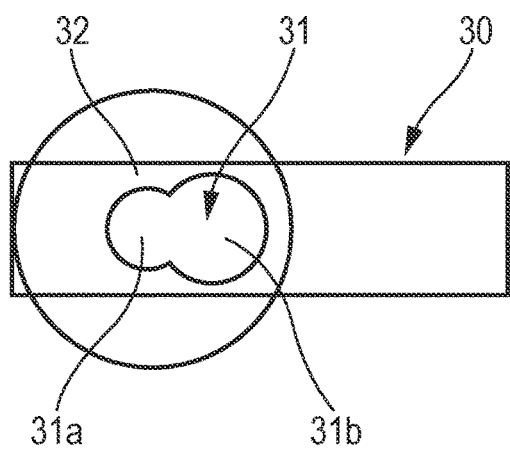
FIG. 3 is a diagrammatic representation of the FIG. 1 device as seen from above.
Figure 4:
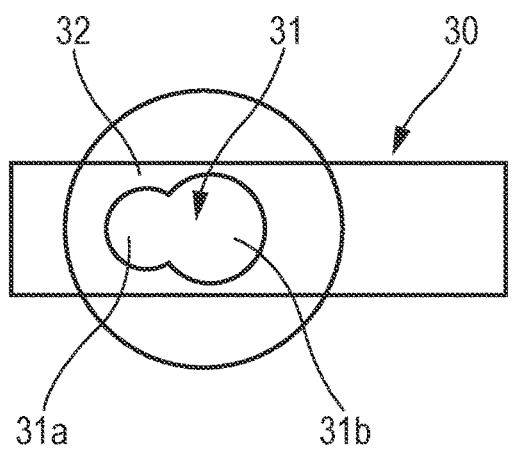
FIG. 4 is a diagrammatic representation of the FIG. 2 device as seen from above.

The opening 31 comprises a first opening portion 31a of smaller size, and a second opening portion 31b of larger size. As can be seen in FIGS. 3 and 4, the first and second opening portions 31a, 31b are interconnected.

Advantageously, the first opening portion 31a may be arranged on one radial side of the plate 30, and the second opening portion 31b may be arranged on the opposite radial side of said plate 30.

In the blocking position, the edge 32 of the first opening portion 31a co-operates with the body 1 so as to hold it in its rest position.

When the plate 30 is moved sideways by the user, the first opening portion 31a is shifted away from the body 1, and once the second opening portion 31b is situated facing the body 1, said body is no longer held by the edge 32 of the first opening portion 31a, and the body 1, together with the reservoir 10, then move axially towards the actuated position under the effect of the compressed spring 20.

This axial movement causes the dose of fluid contained in the reservoir 10 to be dispensed in known manner. Documents EP 0 546 607 and EP 0 311 863 describe devices of the single-dose type in which the dose of fluid is dispensed while the reservoir is moving axially.

In the example in FIGS. 1 to 4, the first and second opening portions 31a, 31b are in the shape of interconnected circles. In a variant, it is possible to have a shape that is generally oblong, widening in regular manner towards the second opening portion 31b. Other shapes can also be envisaged, providing they are interconnected and providing they block the body 1 in the blocking position of the blocking means, and release said body in the non-blocking position.

FIGS. 5 to 13 show a second embodiment, in very diagrammatic manner.

A reservoir 10, containing one or more doses of fluid to be dispensed, is mounted in a base body 2 on which there is assembled a dispenser head 3 provided with a dispenser orifice 4.

During actuation, the reservoir 10 is axially movable relative to the base body 2 and to the dispenser head 3, under the effect of a compressed spring 20 arranged in the base body 2.

In the example shown, the reservoir 10 is fastened in a movable body 41 that is movable both axially in the direction of arrow F1, and also in turning in the direction of arrow F3, see FIGS. 6 to 8. The compressed spring 20 urges the movable body 41 axially upwards, and blocking means 51, 53, 55 are provided so as to prevent said axial movement.

FIGS. 6 to 8 show the movements of the blocking means: each time the movable body 41 is rotating in the direction of arrow F3, one axial stroke takes place in the direction of arrow F1.

FIGS. 9 to 13 show an embodiment example in which the movable body 41 includes a lug 40 that co-operates with axial grooves 52 and 54 that are offset laterally, each axial groove corresponding to dispensing a respective dose. In this example, which has two axial grooves 52, 54, the device is thus of the two-dose type.

Before the first actuation, the lug 40 is offset relative to the first groove 52, and is blocked axially by a first wall 51 of said first groove 52, as can be seen in FIG. 9.

One turn of the movable body moves the lug 40 to face said first groove 52, so that the compressed spring 20 moves said movable body and thus said reservoir 10 axially upwards so as to dispense the first dose, as can be seen in FIG. 10. Said movable body may be turned in either direction, either in the direction of arrow F3, as shown diagrammatically in FIG. 6, or in the opposite direction, as shown in FIGS. 9 and 10.

When the lug 40 reaches the top of the first groove 52, it comes into abutment against a second wall 53 that blocks it axially once again, as can be seen in FIG. 11.

A new turn of the movable body moves the lug 40 to face the second groove 54, as can be seen in FIG. 12, so that the compressed spring 20 moves said movable body and thus said reservoir 10 axially upwards in said second groove 54 so as to dispense the second dose.

When the lug 40 reaches the top of the second groove 54, it comes into abutment against a third wall 55 that blocks it axially once again, as can be seen in FIG. 13.

For a two-dose device, this is the end of the actuation stroke of the device, and the lug 40 is then no longer movable, neither axially, nor in turning.

The present invention thus provides a dispenser device, in particular of the single-dose type or of the two-dose type, that ensures in particular the following functions:

it makes it easier to dispense fluid by lateral actuation, the dispensing of fluid being independent of the user's force, since it is a spring that ensures such dispensing; in particular, the spring guarantees that the spray has characteristics that are constant;

it guarantees that the fluid contained in the reservoir is sealed, before, during, and after actuation of the device;

it enables a prefilled reservoir to be used, so that the device can be assembled in conditions that are not sterile;

it ensures safety in use by enabling doses to be dispensed in any position of the device, and by preventing accidental actuation of the second dose before the first dose has been dispensed; and it limits any risk of contaminating the fluid by putting said fluid in contact with only two materials, namely the material of the reservoir, in general glass, and the material of the piston/stopper, in general an elastomer material that is inert relative to the fluid.

Naturally, as described above at the beginning of the description, the present invention is not limited to devices of the single-dose type or of the two-dose type, nor is it limited to devices of the nasal type. By way of example, it is possible to envisage such a device for dispensing three or four doses, e.g. in the user's eyes, ears, or mouth.

The invention claimed is:

1. A fluid dispenser device comprising: a reservoir (10) containing one or more doses of fluid; a resilient element (20), such as a spring, for urging said reservoir (10) to move axially between a rest position and at least one actuated position; and blocking means (30; 51, 53, 55) for preventing said reservoir (10) from moving axially; said blocking means being movable manually in a direction that is different from the direction of said axial movement of the reservoir (10) so as to allow said reservoir (10) to move axially; wherein said blocking means comprise a plate (30) provided with an opening (31) comprising a first opening portion (31a) of smaller size, and a second opening portion (31b) of larger size, said first and second opening portions (31a, 31b) being interconnected at an interconnection portion, with said first opening portion extending exclusively on one side of said interconnection portion and said second opening portion extending exclusively on another ide of said interconnection portion, said plate (30) being movable radially between a blocking position in which said first opening portion (31a) co-operates with said reservoir (10) so as to block said reservoir axially, and a non-blocking position in which said second opening portion (31b) co-operates with said reservoir (10) so as to allow said reservoir (10) to move axially under the effect of said resilient element (20).

2. A device according to claim 1, wherein said reservoir (10) is fastened in a body (1), said opening (31) of said plate (30) receiving said body (1) and the edges of said opening (31) co-operating with said body (1).

3. A device according to claim 1, wherein said first and second opening portions (31a, 31b) are in the shape of interconnected circles.

4. A device according to claim 1, wherein said reservoir (10) contains a dose of fluid for dispensing in a single actuation.

5. A device according to claim 1, wherein said reservoir (10) contains two doses of fluid for dispensing in two successive actuations.

6. The device according to claim 1, wherein said first and second opening portions have a fixed geometry that remains the same when the plate is moved from the blocking position to the non-blocking position.

7. The device according to claim 6, wherein said first and second opening portions are in the shape of interconnected circles.

8. The device according to claim 6, wherein said first and second opening portions are interconnected and permanently spaced relative to one another along the direction of movement of the blocking means.

\* \* \* \* \*